(12) United States Patent
Alstad et al.

(10) Patent No.: US 8,370,089 B2
(45) Date of Patent: Feb. 5, 2013

(54) METHOD AND EQUIPMENT FOR DETERMINING THE INTERFACE BETWEEN TWO OR MORE FLUID PHASES

(75) Inventors: Vidar Alstad, Porsgrunn (NO); Robert Aasheim, Porsgrunn (NO); Kjetil Fjalestad, Skien (NO); Truls Fallet, Oslo (NO)

(73) Assignee: Statoil ASA, Stavanger (NO)

( * ) Notice: Subject to any disclaimer, the term of this patent is extended or adjusted under 35 U.S.C. 154(b) by 225 days.

(21) Appl. No.: 12/808,069

(22) PCT Filed: Dec. 17, 2008

(86) PCT No.: PCT/NO2008/000458
§ 371 (c)(1),
(2), (4) Date: Jun. 14, 2010

(87) PCT Pub. No.: WO2009/078734
PCT Pub. Date: Jun. 25, 2009

(65) Prior Publication Data
US 2010/0262387 A1    Oct. 14, 2010

(30) Foreign Application Priority Data
Dec. 19, 2007 (NO) .................................. 20076551

(51) Int. Cl.
*G01F 23/00* (2006.01)
*G01F 25/00* (2006.01)
(52) U.S. Cl. ........... 702/55; 702/100; 702/182; 702/188
(58) Field of Classification Search ............. 702/55–57, 702/66, 67, 100, 182–189
See application file for complete search history.

(56) References Cited

U.S. PATENT DOCUMENTS
5,325,716 A * 7/1994 Hafner et al. ................... 73/301
2003/0005747 A1 * 1/2003 van der Geest et al. ....... 73/1.16

FOREIGN PATENT DOCUMENTS
| CN | 1493878 A | 5/2004 |
| JP | 06194207 A | 7/1994 |
| JP | 8193867 A | 7/1996 |
| RU | 2188396 C2 | 8/2002 |
| RU | 2236584 C1 | 9/2004 |
| RU | 2277635 C2 | 1/2006 |

OTHER PUBLICATIONS

Lees, Raymond Paul "Increase Oil Production and Reduce Chemical Usage Through Separator Level Measurement by Density Profiling" ISA Emerging Technologies Conference, 2005.

* cited by examiner

*Primary Examiner* — Phuong Huynh
(74) *Attorney, Agent, or Firm* — Volpe and Koenig, P.C.

(57) ABSTRACT

A method and equipment are provided for determining the level/height, of one or more interfaces between two or more fluid phases of different density that are contained in a vessel, tank or the like. The position of the different interfaces in a tank is determined by measuring the pressure thereby determining the density of the fluid over the height of the tank by using a pressure measuring rod, equipped with pressure sensors, positioned in the tank. A mathematical model or algorithm is used which calculates how the density and hence the pressure vary over the height of the tank as a function of the fluid properties of the respective fluids in the tank, the interface, on the basis of the density being the same within each layer of the respective fluid, as a respective point at which the density changes from one layer to the next in the tank.

12 Claims, 6 Drawing Sheets

METHOD AND EQUIPMENT FOR DETERMINING THE INTERFACE BETWEEN TWO OR MORE FLUID PHASES

The present invention relates to a method and equipment for determining (measuring) the level/height of one or more interphase borders/interfaces between two or more fluid phases of different density that are contained in a vessel (tank).

In oil processing plants, whether subsea, offshore or onshore, the separation process is important. During this process, water, oil and gas that are produced from the wells in the oil field are separated. To obtain the right quality of the different (fluid) phases from the separator, it is essential at all times to know exactly where the interface between each phase is located within the separation tank. In addition, it is important to know where the level of each individual fluid is in order to prevent the tank from being filled or emptied. Inaccurate level measurements can result in large production losses and reduced product quality. They may also lead to undesirable emissions into the environment.

Experience from a number of gas and oil fields shows that there is a need for better methods and equipment for determining the different levels that are found in the separation tank. A more exact indication of the interfaces will help to increase both production and operating life for numerous plants.

The interface between two phases (for example, oil and water) is determined on the basis that the phases have different physical properties. Various instruments are able to detect where these properties change, and consequently the interfaces in the tank can be indicated.

However, this is difficult to do in practice, and commercial measuring instruments do not have the desired robustness and precision. The problem is greatest in heavy oil plants and where there is substantial oil-water emulsion with a gradual transition between the phases that are to be separated. Furthermore, the instruments require a great deal of space, and extensive calibration is necessary.

In addition, the best instruments today are based on radioactive sources which call for special handling.

An overview of the most common measuring principles is given by Bukhari, S. F. A and Yang, W., "Multi-interface Level Sensors and New Development in Monitoring and Control of Oil Separators", Sensors 2006, 6, pages 380-389.

The existing methods for measuring level (interface between phases) are based on detecting the position at which changes in the properties of the media being measured take place. In the case of existing measuring instruments (ref. Tracerco profiles), information from two sensor elements is used to determine where the interface is. The elements will vary depending on the position of interface.

GB-A-2236688 describes a method in which a rod with two or three pressure sensors is used to regulate the level in a separator. The use of this method requires extensive calibration before the start-up of the plant. In order to carry out the calibration, the density of the different phases must be known. The method is completely dependent on each sensor giving sufficiently precise measurements and on there being no change in the density in the phases. If there is a drift in a measurement (over time) or the density changes, it will indicate the wrong level.

The object of the present invention was to arrive at a more precise method and equipment than those mentioned above to find the level (interphase border or interface) between two or more phases that are contained in a vessel.

The method according to the invention is characterised by the features that are disclosed in attached independent claim 1.

Furthermore, the equipment is characterised by the features that are disclosed in attached independent claim 5.

Dependent claims 2-4 and 6-10 disclose advantageous features of the invention.

The invention will be described in more detail below with the aid of an example and with reference to the figures wherein.

The term "relatively similar density" as used here refers to the density of a fluid measured at several measuring points distributed over the height of the fluid layer being the same when any concentration gradients in relation to the other fluid or fluids present in the tank are disregarded.

The inventors found that the position of the different interfaces in a tank can be determined in a more precise way by measuring the pressure and thus indirectly determining the density of the fluid in the tank over the height of the tank. This, combined with a mathematical model of how the density and hence the pressure vary over the height of the tank as a function of fluid properties, makes it possible to find the interfaces for the different phases by minimising the difference between estimated pressure from the model and measured pressure. The method according to the invention uses more information (several measuring points) than strictly necessary in order to find the position of the interfaces. This makes the method robust against errors from individual measurements and other noise, and distinguishes it from other previously proposed methods/instruments.

Figure 1:
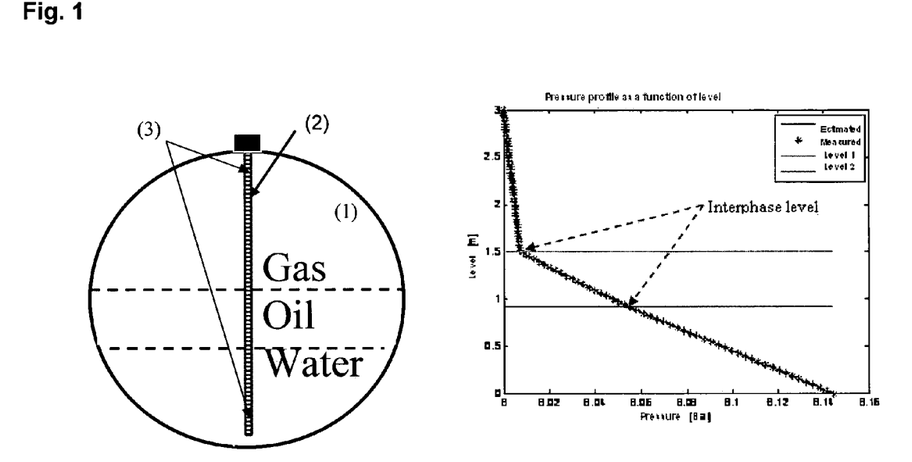
FIG. 1 shows a separator with a segment-based pressure measuring rod equipped with sensors according to the invention, and a curve on the right representing an associated pressure profile.

As shown in FIG. 1, the basis of the method is that a support in the form of a pressure measuring rod 2 equipped with pressure sensors 3 is positioned vertically in and extends over the height of a tank 1 (separator body) where the position of the interface is to be measured. The figure shows a system with gas, oil and water, but the principle is suitable for all tanks containing two or more phases of different density. The support has many small pressure sensors distributed along its length; for example, spaced 1 cm apart. The distribution of the sensors may be uniform, but is not limited to this. The support must be positioned so that each fluid phase surrounds several sensors (thereby enabling the level and the density to be measured), and the distance between each sensor must be known. Consequently, it is not necessary that the pressure measuring rod should extend over the whole of the height of the tank.

The method according to the invention can also be used to find the position of interfaces based on measuring principles other than pressure. Measuring principles which directly or indirectly say something about one or more characteristic properties of the fluids can be used to find the interface between the fluids. Examples of such measuring principles are radioactive sources/receivers, temperature, capacitance, resistivity, pressure, or combinations of such measuring principles.

To determine the interface between each phase, all or a selection of the pressure measurements from the sensors are used. An algorithm, as described below, finds the areas along the support which have the same density, and when the density changes this means that an interface is detected. If there are three phases in a separator, this means that the algorithm is to find two interfaces. In the cases where there may be foam or emulsions, several interfaces may be determined.

It is assumed in the mathematical model that the density is the same within each layer in the separator. This means that the interface between each phase is given on the basis of the height at which the density changes. Moreover, it is assumed that the density within each phase may vary over time.

In addition to the levels (the interface), the densities of the different phases can also be calculated. This is done on the basis of the estimated slope of the pressure profile. This means that the density in one or more phases can be determined even though it changes over time. The result of this is that the instrument is self-calibrating.

If there is a gliding transition between the phases (e.g., in emulsions and foam), this can be calculated by finding several changes in the slope of the pressure profile.

To be able to calculate the levels of emulsions, sufficiently many and precise pressure measurements are required. In other words, it is necessary that more than one pressure measurement is located in the emulsion layer, and these must be sufficiently accurate to be able to indicate a change in the slope of the pressure profile. With multiple sensors in layers of emulsions/foam, the requirement of accuracy is reduced.

In gravitation-based separation processes, the heaviest phase will fall to the bottom, and the lightest phase will rise to the top.

Figure 2:
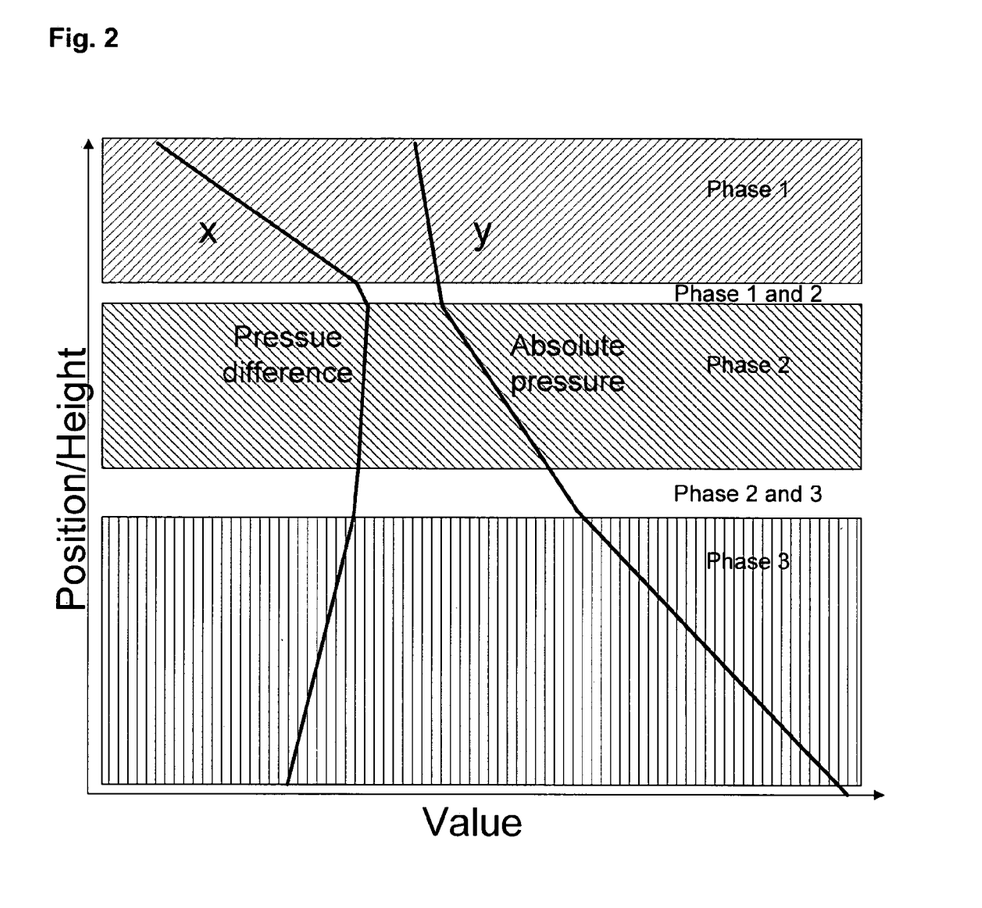
FIG. 2 shows an illustration of the cross-section of a tank containing 3 phases where the pressure difference (x) and absolute pressure (y) vary according to the height, h, in a separator.

When the density and the interfaces are to be calculated, this fact can be utilised so that an absolute pressure profile always has least slope at the top, with the slope increasing towards the bottom, as shown in FIG. 2. This is utilised in the algorithm in order to eliminate errors, and can also be utilised in cases where differential pressure is used.

To determine the position of the interface between each phase, there is used, as mentioned above, the principle that the density of the media can be measured indirectly through pressure measurements over the height of the separator. In addition, there is used a mathematical model of how the measured pressure is related to the density by which it is desired to distinguish the phases.

FIG. 2 indicates a pressure profile and a differential pressure profile over a tank where there are several phases of different density. Measurement of pressure difference between process medium and reference medium is shown by the x curve, whilst absolute pressure/gauge pressure is shown by the y curve.

It is desirable to find at which vertical position/height the density changes. For each pressure sensor, the following physical consideration applies:

$$p_{i+1} = \rho_i g \Delta h_i + p_i \quad (1)$$

where $p_i$ is the pressure at sensor no. i,
$\rho_i$ is the density between sensor no. i and sensor no. i+1,
$\Delta h_i$ is the vertical distance between sensor no. i and sensor no. i+1,
g is the gravitation.

This means that the density is given by:

$$\rho_i = \frac{1}{g \Delta h_i}(p_{i+1} - p_i) = k \Delta p_i \quad (2)$$

where $\Delta p_i$ is the pressure difference between sensor no. i and sensor no. i+1,
k is a constant given by g and $\Delta h_i$.

By allowing the density at a given position "i" to be given by $\rho_i$, the density can then be determined by a mathematical function $$\hat{\rho} = f_\rho(h, u) \quad (3)$$

where $\hat{\rho}$ is the estimate of the density $\rho$, h is a measurement of position (the height) in the tank and $f_\rho(\cdot)$ is a mathematical function (description) of the density and how it depends on h and u. $f_\rho(\cdot)$ can be determined on the basis of equation (2) where $p_i$ is the pressure at level $h_i$, u is a vector of parameters/variables that are to be determined. Typical variables in u are the heights at which there is a transition from one phase to another and the densities of each fluid phase. The function $f_\rho(\cdot)$ may be based on a physical model of the relation between height and the density (as in equation (1)) and optionally other parameters it is desirable to find. The function in equation (3) is explicit, but a general implicit function in the properties can also be used.

The estimate of this measured pressure or differential pressure in a position h is:

$$\hat{P} = f_P(\hat{\rho}, h, u) \quad (4)$$

where $f_P(\cdot)$ is a function that indicates the relation between density and pressure over the height of the tank, $\hat{\rho}$ is the estimate of the density that it is desirable to know and u is a vector (several values) of parameters/variables that it is desired to determine. $f_P(\cdot)$ can be determined on the basis of equation (1). The description does not need to be explicit here either.

The position of the interfaces affects the density over the cross-section and this is observed in the measured pressure.

In the majority of cases, discrete measurements of the pressure over the cross-section of the tank are obtained, so that the discrete relations are $$\hat{\rho}_i = f_\rho(h_i, u) \quad (5)$$

and $$\hat{P}_i = f_P(\hat{\rho}_i, h_i, u) \quad (6)$$

where "i" is the discretisation point (each "i" corresponds to the given height/vertical position of sensor no. i). The distribution of measuring points does not need to be uniform over the height, but the distance between each measuring point must be known.

Based on distributed measurements of the pressure over measured height, it is desirable to find where the transitions between the phases are. That is to say, it is desirable to find all the positions $h^{m,n}$ that are the height in the tank between phase "m" and "n". In addition, the other variables that are necessary in order to describe the relation between measured pressure and density that is to distinguish between the phases must be found. These are included in the vector u.

These positions are not limited to points for which there are measurements of pressure (may also be a height between two discretisation points).

Based on the mathematical models $f_\rho(\cdot)$ and $f_P(\cdot)$, the levels and the densities (i.e., u) can be found by minimising the difference between P and $\hat{P}$ which can be expressed $$u = \arg\min_u \|P - \hat{P}(u, \cdot)\| \tag{7}$$

where $\hat{P}$ is estimated pressure from the model in equations (5) and (6) and P is the measured pressure value, $\|\cdot\|$ is a norm or measure of the distance between the model's predictions and what is measured. E.g., the least squares method can be used to solve the problem above, but the invention is not limited to this. Another possible method is to use a Kalman filter.

This differs essentially from previous principles for measuring interfaces in that more information than necessary is used to estimate the interfaces and a model which is used in the algorithm where a difference between measured and estimated property is minimised in order to find the interfaces.

For N parameters to be determined (i.e., that the vector u consists of N values) on the basis of equation (7), it is necessary to have at least N pressure measurements. In practice, it is desirable to have more measurements than variables in u in order to obtain an overdefined system, and thus be able to determine the parameters (i.e., interface level and densities) more accurately.

Example: It is desirable to find where the density changes in a tank containing three phases (water, oil and gas). The position at which the density changes indicates where the interface is. It is therefore assumed that a measurement is made of the pressure over the cross-section (e.g. as discrete points). $\rho$ is density [kg/m³] and P is the pressure [Pa]. Let $h^{g,o}=h^2$ and $h^{o,w}=h^1$ be the true levels of the interface between, respectively, gas/oil and oil/water that it is desired to find. In the model of how the density changes, it is assumed that the density is constant in each phase (and that there is a pure phase on each side of the interface). The functions are then $$\hat{\rho}(h_i, [h^1 \ h^2]) = f_\rho = \begin{cases} \rho_g & \text{for } h^2 < h_i < h^+ \\ \rho_o & \text{for } h^1 < h_i < h^2 \\ \rho_w & \text{for } h^- < h_i < h^1 \end{cases} \tag{8}$$

where $h^-$ and $h^+$ are respectively a bottom reference and a top reference. The estimated pressure $\hat{P}$ at a point "i=n" in the tank is:

$$\hat{P}_i(h_i, [h^1 \ h^2]) = \begin{cases} \rho_g g(h^+ - h_i) & \text{for } h^2 < h_i < h^+ \\ \rho_g g(h^+ - h^2) + \\ \rho_o g(h^+ - h_i) & \text{for } h^1 < h_i < h^2 \\ \rho_g g(h^+ - h^2) + \\ \rho_o g(h^+ - h^1) + & \text{for } h^- < h_i < h^1 \\ \rho_w g(h^+ - h_i) \end{cases} \tag{9}$$

where g is the gravitation constant.

Here it is assumed that the pressure profile can be described as straight lines (assuming that the density is not a function of the height). In the general case, it can thus be written:

$$\hat{P} = a\left(\rho_0 h - \sum_{j=1}^{N} \Delta\rho^j \max(h - h^j, 0)\right) \tag{10}$$

where
P is a vector of pressure at each of the sensors,
h is a vector of the level (the height) of each of the sensors,
$\rho_0$ is the density of the heaviest phase $\Delta\rho^j$ is the change in density between two phases (here it must be so that $\Delta\rho^j > 0$)
$h^j$ is the level (the height) of the interface between two phases (here must be so that $h^{j+1} > h^j$)
a is a conversion factor that takes into account gravitation and units of measurement
N is the number of interfaces to be determined The function consists of N+1 straight lines that are put together.

It is now desirable to find 2 interfaces $h^2=h^{g,o}$ and $h^1=h^{o,w}$. To be able to find them, the densities of each of the phases must also be found so that we have $u=\lfloor h^1 \ h^2 \ \Delta\rho^1 \ \Delta\rho^2 \ \rho_0 \rfloor$ This is found by solving $$[h^1 \ h^2 \ \Delta\rho^1 \ \Delta\rho^2 \ \rho_0] = \tag{11}$$
$$\arg\min_{[h^1 \ h^2 \ \Delta\rho^1 \ \Delta\rho^2 \ \rho_0]} \|P - \hat{P}([h^1 \ h^2 \ \Delta\rho^1 \ \Delta\rho^2 \ \rho_0])\|$$

where a difference between the measured (P) and the estimated ($\hat{P}$) is minimised by changing the parameters ($u=\lfloor h^1 \ h^2 \ \Delta\rho^1 \ \Delta\rho^2 \ \rho_0 \rfloor$).

In the calculations here it can be seen that distributed information from the whole profile (measuring area) is used to determine the interfaces. This results in greater robustness against erroneous measurements than in the previously used level measurement methods. In addition, it is not necessary to know the density of the phases as they are estimated in the algorithm together with the levels. If it is desirable, the density can be specified and the position of the interfaces found alone.

Here, it has been assumed that the relation between density and pressure can be described as a straight line within each phase. The algorithm is not limited to this, e.g., a non-linear relation could be used for the oil phase (which consists of many chemical components of different density).

To increase the robustness of the algorithm, limitations for what is a valid solution can be inserted. E.g., but not limited to this, the position of the gas/oil interface must be higher than the oil/water contact. In addition, density must increase downwards in the tank.

As mentioned above and as shown in FIG. 1, the method and the equipment according to the present invention are based on a support 2 equipped with sensors 3 being positioned vertically in and extending over the height of a tank 1 (separator body) in which the position of the interface is to be measured. The figure shows a system with gas, oil and water, but the principle is suitable for all tanks containing two or more phases of different density. The support that may be a rod made of a material that has sufficient strength and heat resistance, that is chemically unaffected, and that has many small pressure sensors distributed along the whole of its length; for example, at a distance of 1 cm. The distribution of the sensors may be uniform, but is not limited to this. The support must be so positioned in a measuring situation that each fluid phase surrounds several sensors, and the distance between each sensor must be known.

Figure 3:
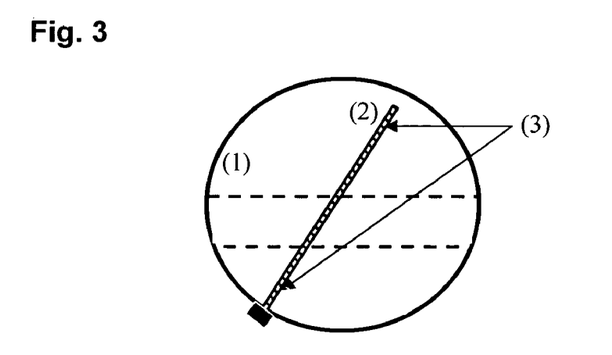
FIGS. 3-5 show alternative designs and positions of a segment-based pressure measuring rod in a tank or flange of a tank.
Figure 4:
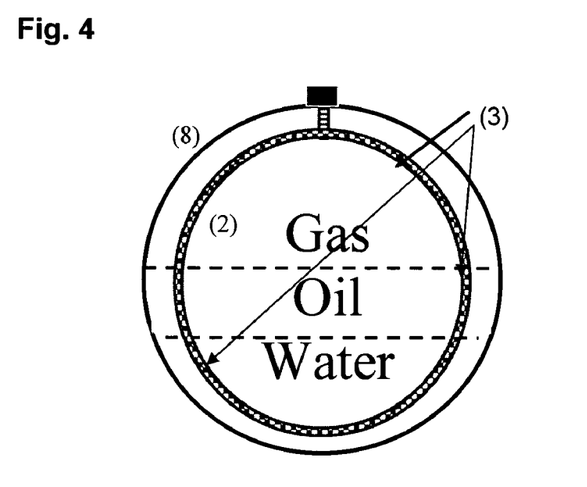
Figure 5:
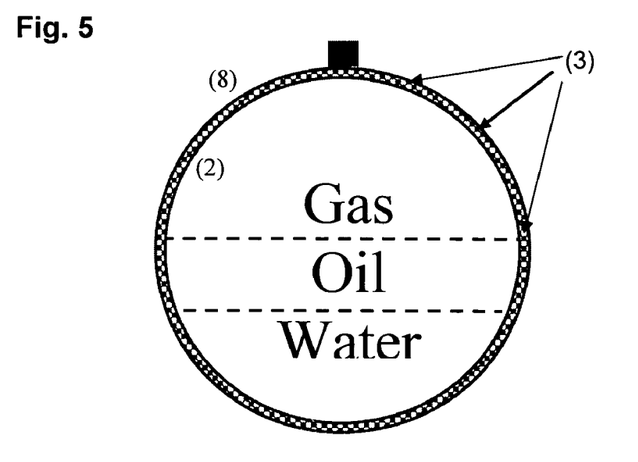

FIG. 1 shows an example of a straight support, i.e., a measuring rod which extends in a vertical line from the bottom to the top of a tank. However, the invention is not limited to such a solution. Thus, the support may have any other position and configuration, e.g., as shown in FIG. 3 where the support is an inclined rod arranged in a tank, FIG. 4 where the support consists of a circular measuring rod positioned inside a tank, or as shown in FIG. 5 where the support is circular, but adapted to be arranged, e.g., in a flange of a tank.

To make the system flexible, the support may be built up of modules (for example, 1 metre long) that are put together. Different modules can be made which are either straight or curved, so that the sensor support is given the desired configuration. Thus, the sensor support can also be mounted from different sides of the tank. The support may extend over parts of or the whole of the height of the vessel. A cable (not shown in any detail) is run from the support for signal and power transmission, and this cable runs through a flange which is not necessarily located immediately adjacent to the sensor support. This makes the measuring instrument flexible as regards both structure and position. If there is a need, several separate supports may be positioned in a separator and the cables from all the rods can pass through the same flange.

The sensors used, like the measuring rod, must be capable of withstanding the relevant process pressure and temperature. The process pressure may be up to at least 100 bar, and in the case of sensors that are to be used in a subsea situation, they should be able to withstand a pressure of up to about 2-400 bar. At the same time, the sensors must function for temperatures as high as at least 200° C. The sensors should otherwise be able to measure the pressure with an accuracy in the order of 100 Pa (i.e., 0.01 mBar), but also less accurate sensors can be used because the accuracy can be enhanced by the algorithm that finds the levels.

Figure 6:
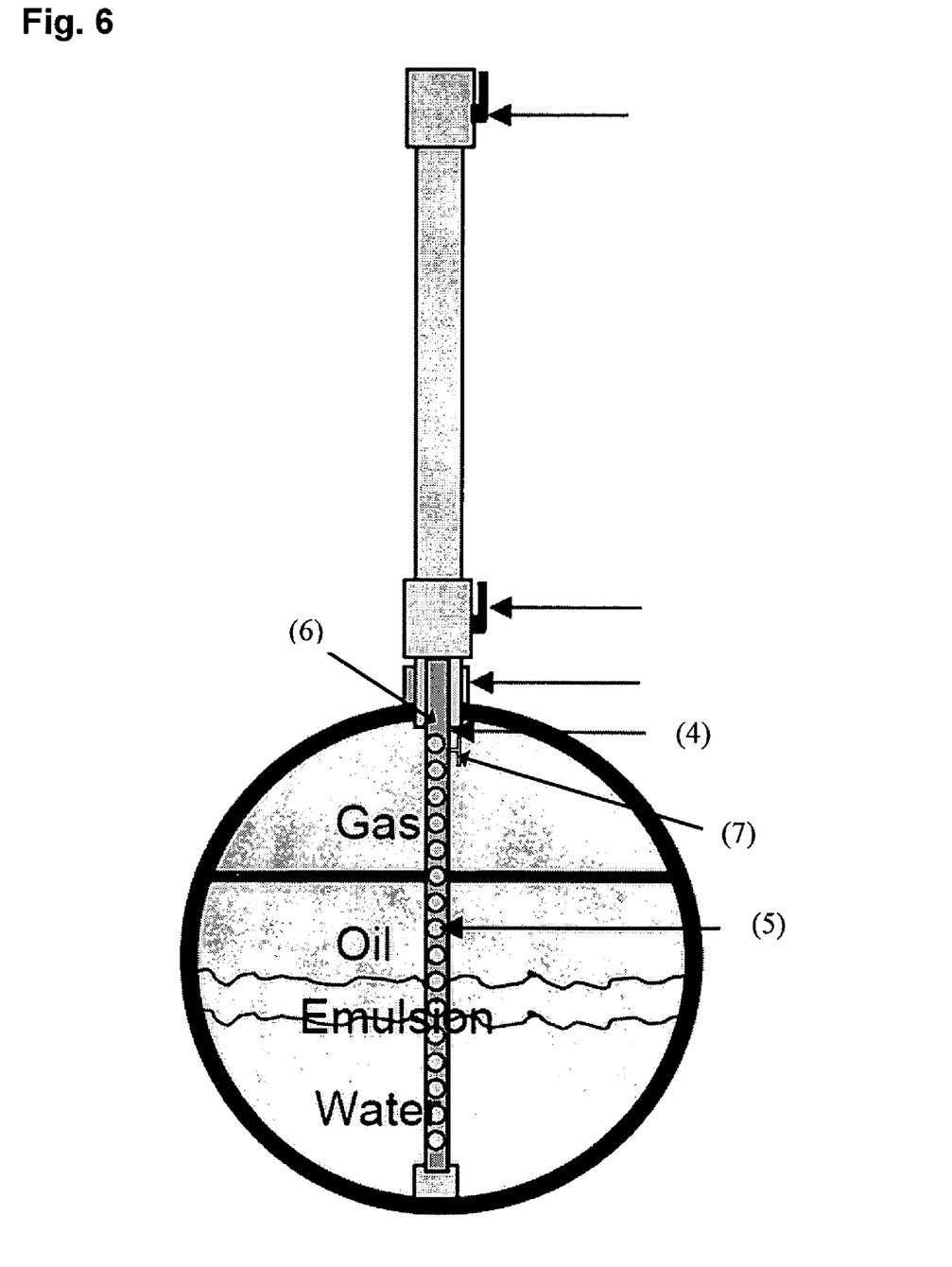
FIG. 6 shows a modified pressure measuring rod for measuring differential pressure between a process medium and a reference medium.

To be able to calculate an interface/level in a separator with good accuracy, the pressure measurements on the basis of which the level is calculated are required to have sufficient accuracy. For situations (for example, processes) where pressures are high, it is difficult to find pressure sensors that have the desired precision. It is possible to solve this by using differential pressure measurements between the medium in the tank and a reference medium (for example, silicone oil) as shown in FIG. 6, instead of using absolute pressure measurements as shown in FIG. 1. This gives a differential pressure profile vertically in the tank (or the separator) which forms a basis for determining the interfaces.

The equipment according to the invention will then in a modified pressure difference version consist of three main parts:
1. A support equipped with differential pressure sensors where the number and position must be such that there are two or more sensors in each phase (if the density is not known), and in total there are more sensors than parameters that are to be determined.
2. A parallel support which has a reference fluid across the length of the support where the density is constant. For example, there may be a chamber within the differential pressure support over the height of the sensor which is filled with a reference medium of known density. The reference medium may also be sectioned over the height of the support, but all reference media must be pressure-balanced against the process medium. To obtain a more precise pressure measurement, the difference in pressure between the process medium and the reference medium is measured, instead of measuring absolute pressure.
3. A mathematical model or algorithm for determining the interfaces (and the densities) on the basis of the pressure profile.

FIG. 6 shows the modified version of the invention where the solution is exemplified by differential pressure measuring rod 4 equipped with differential pressure sensors 5 arranged along the length of the rod. The measuring rod has a cavity 6 in its longitudinal direction that is filled with reference fluid, the sensors that are arranged in the wall of the measuring rod being adapted to measure differential pressure between the process medium outside (e.g, oil, water, gas) and the reference fluid. A pressure equalising membrane between the reference fluid and the process medium outside is arranged uppermost in the measuring rod (not shown in any detail).

Figure 7:
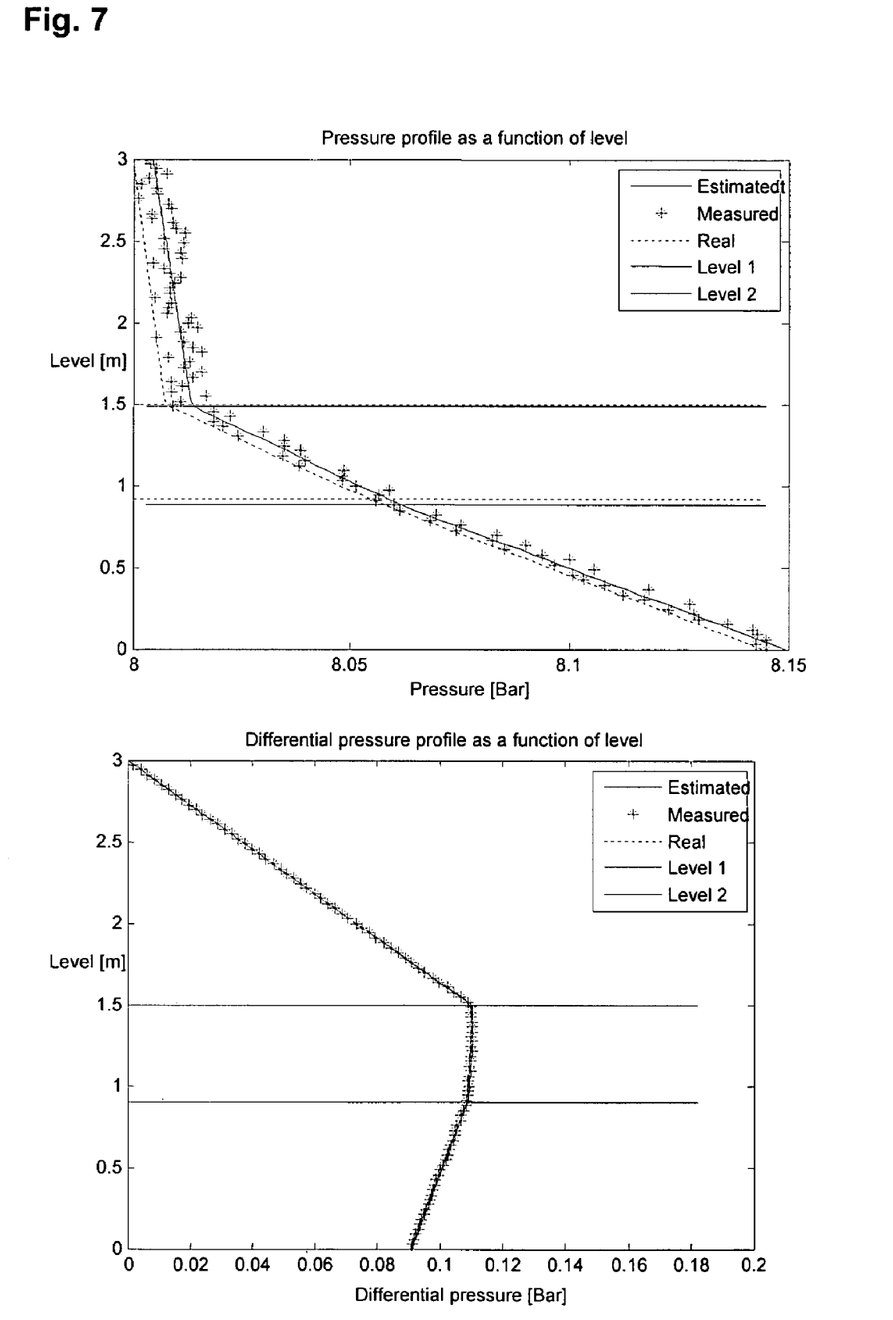
FIG. 7 shows a pressure profile for measurements based on absolute pressure (at the top) and based on reference pressure (at the bottom).

FIG. 7 shows the pressure profiles from measurements using absolute sensors (at the top) and the differential pressure profile (at the bottom). The modified measuring principle, as can be seen from the figures, gives more accurate pressure measurements and a better determination of the layers.

In the top figure it is easy to see one of the interfaces (oil/gas), but difficult to see the other (water/oil) where a change in the slope is smaller. Both layers are clearer in the lowermost figure where the profile is based on differential pressure. The same mathematical algorithms can be used for both cases.

Figure 8:
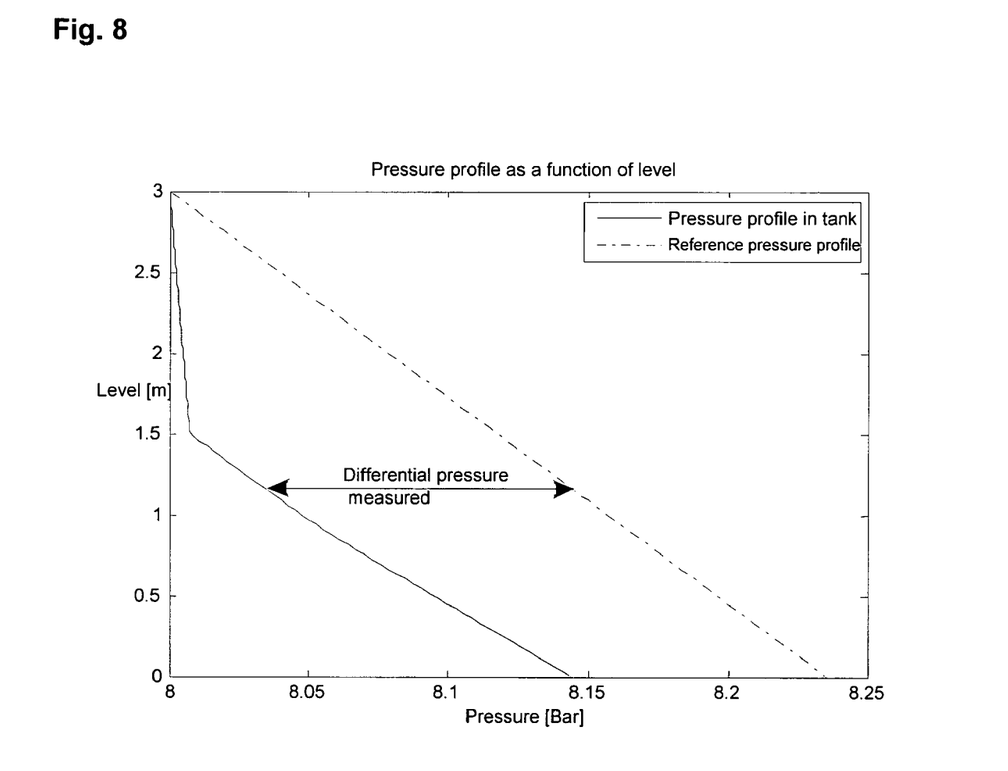
FIG. 8 shows the relation between absolute pressure, reference pressure and differential pressure.

FIG. 8 shows the relation between absolute pressure measurements, the reference pressure and the measured differential pressures.

The densities of the different phases can also be calculated in, both cases. This is done on the basis of the slope of the pressure profile, optionally on the basis of the difference in the slope of the measured differential pressure profile and the known density of the reference medium in the rod.

If there is a gliding transition between some of the phases (e.g., where there are emulsions and foam), this is easier to determine using the differential pressure sensor as described in connection with FIG. 6.

The invention as defined in the claims is not limited to the examples described in the above. Thus, a similar algorithm can be used for types of measurements other than pressure (for example, density) where there are more measurements than variables that are to be determined. By indicating a relation between physical variables that are to be determined and what is measured, the system is overdefined and this increases both robustness and precision of the measuring method.

The invention claimed is:
1. A method for determining (measuring) the level/height of one or more interfaces, $h_1$-$h_x$, between two or more fluids/process media (fluid phases) of different density that are contained in a vessel or a tank (1) the method comprising:
   determining the position (the level) of the different interfaces in a tank (1) by measuring the pressure and thus indirectly determining the density of the fluid over the height of the tank
   positioning a pressure measuring rod (2, 4), equipped with pressure sensors (3, 5), in and extending over the height of the tank (1), to determine the position of the different interfaces wherein, there are more pressure sensors and pressure measurements than the number of variables that are to be determined, so that the system is overdefined and thus more robust,
   determining the interfaces using a mathematical model or algorithm which calculates how the density and hence the pressure vary over the height of the tank as a function of the fluid properties of the respective fluids in the tank, the interface, on the basis of the density being relatively similar within each layer of the respective fluid, being defined as the respective point (level) at which the density changes from one layer to the next in the tank.

2. A method according to claim 1, wherein the respective interfaces, $h_1$-$h_x$, are determined through the use of the following algorithm by minimising the difference between:

$$u = \underset{u}{\operatorname{argmin}} \| P - \hat{P}(u, \cdot) \|$$

where u in the algorithm is a vector of variables that are to be determined, P is a vector of measured pressure and $\hat{P}$ is calculated pressure based on the variables in the vector u.

3. A method according to claim 2, wherein the algorithm is based on the least squares method or a Kalman filter.

4. Equipment for determining the level/height of one or more interphase borders/interfaces, $h_1$-$h_x$, between two or more fluids/process media (fluid phases) of different density that are contained in a vessel or a tank (1), comprising
   a unit for measuring/recording a state in the tank and a second unit for determining the position (level) of the interface(s), wherein the equipment is based on the position of the different interfaces, $h_1$-$h_x$, being determined by measuring the pressure and thus indirectly determining the density of the fluid in the tank over the height of the tank using
      a pressure measuring rod (2) equipped with pressure sensors (3) distributed along the whole length of the rod, and which is adapted to be positioned vertically in and extend over the height of the vessel (1) where the position of the interfaces is to be measured, wherein there are more pressure sensors and pressure measurements than the number of variables that are to be determined, so that the system is overdefined and thus more robust.

5. Equipment according to claim 4, wherein the pressure that is measured/recorded is a differential pressure between the process medium and a reference fluid, the differential pressure being measured/recorded by a differential pressure measuring rod (4) equipped with differential pressure sensors (5) arranged along the length of the rod.

6. Equipment according to claim 5, wherein the measuring rod has a cavity (6) in its longitudinal direction that is filled with reference fluid, the differential pressure sensors being arranged in the wall of the measuring rod (4) and adapted to measure the differential pressure between the process medium outside and the reference fluid in the cavity (6), a pressure equalising membrane (7) being arranged in connection with the differential pressure measuring rod between the reference fluid and the process medium outside.

7. Equipment according to claim 5, wherein the measuring rod (2, 4) comprises an elongate body and is adapted to be arranged vertically or aslant in the tank (1).

8. Equipment according to claim 5, wherein the measuring rod (2, 4) is arranged in connection with a substantially circular body (8) which is adapted to be positioned along the periphery of the tank (1).

9. Equipment according to claim 5, wherein the measuring rod (2, 4) is arranged in connection with a substantially circular body (8) that is adapted to be positioned in a flange of the tank (1).

10. Equipment according to claim 6, wherein the measuring rod (2, 4) comprises an elongate body and is adapted to be arranged vertically or aslant in the tank (1).

11. Equipment according to claim 6, wherein the measuring rod (2, 4) is arranged in connection with a substantially circular body (8) which is adapted to be positioned along the periphery of the tank (1).

12. Equipment according to claim 6, wherein the measuring rod (2, 4) is arranged in connection with a substantially circular body (8) that is adapted to be positioned in a flange of the tank (1).

* * * * *